US007923002B2

(12) United States Patent
De La Poterie et al.

(10) Patent No.: US 7,923,002 B2
(45) Date of Patent: *Apr. 12, 2011

(54) COMPOSITION FOR COATING KERATIN FIBRES COMPRISING A TACKY WAX

(75) Inventors: Valérie De La Poterie, Le Chatelet en Brie (FR); Thérèse Daubige, Mousseaux les Bray (FR); Patrice Styczen, Gif-sur-Yvette (FR)

(73) Assignee: L'Oreal S.A., Paris (FR)

( * ) Notice: Subject to any disclaimer, the term of this patent is extended or adjusted under 35 U.S.C. 154(b) by 1495 days.

This patent is subject to a terminal disclaimer.

(21) Appl. No.: 10/654,887

(22) Filed: Sep. 5, 2003

(65) Prior Publication Data

US 2004/0137020 A1 Jul. 15, 2004

Related U.S. Application Data

(60) Provisional application No. 60/412,854, filed on Sep. 24, 2002, provisional application No. 60/418,345, filed on Oct. 16, 2002, provisional application No. 60/418,357, filed on Oct. 16, 2002, provisional application No. 60/412,853, filed on Sep. 24, 2002, provisional application No. 60/412,855, filed on Sep. 24, 2002.

(30) Foreign Application Priority Data

| Sep. 6, 2002 | (FR) | 02 11096 |
| Sep. 6, 2002 | (FR) | 02 11097 |
| Sep. 6, 2002 | (FR) | 02 11104 |
| Sep. 30, 2002 | (FR) | 02 12097 |
| Sep. 30, 2002 | (FR) | 02 12098 |

(51) Int. Cl.
*A61Q 1/10* (2006.01)
(52) U.S. Cl. ......................... 424/70.7; 424/401
(58) Field of Classification Search .................. None
See application file for complete search history.

(56) References Cited

U.S. PATENT DOCUMENTS

| 3,673,160 A | 6/1972 | Buisson et al. |
| 3,802,841 A | 4/1974 | Robin |
| 3,937,811 A | 2/1976 | Papantoniou et al. |
| 4,887,622 A | 12/1989 | Gueret |
| 5,156,911 A | 10/1992 | Stewart |
| 5,159,052 A | 10/1992 | Barthelemy et al. |
| 5,356,627 A | 10/1994 | Da Cunha et al. |
| 5,429,816 A | 7/1995 | Hofrichter et al. |
| 5,472,798 A | 12/1995 | Kumazawa et al. |
| 5,519,063 A | 5/1996 | Mondet et al. |
| 5,591,424 A | 1/1997 | Hofrichter et al. |
| 5,650,144 A | 7/1997 | Hofrichter et al. |
| 5,736,125 A | 4/1998 | Morawsky et al. |
| 5,747,013 A | 5/1998 | Mougin et al. |
| 5,756,635 A | 5/1998 | Michaud et al. |
| 5,783,176 A * | 7/1998 | Meiring et al. .................. 424/64 |
| 5,858,338 A | 1/1999 | Piot et al. |
| 5,860,432 A | 1/1999 | Gueret |
| 5,894,847 A | 4/1999 | Gueret |
| 5,925,337 A | 7/1999 | Arraudeau et al. |
| 5,934,292 A | 8/1999 | Gueret |
| 5,985,298 A * | 11/1999 | Brieva et al. .................. 424/401 |
| 6,099,183 A | 8/2000 | Gueret |
| 6,103,221 A | 8/2000 | Arnaud et al. |
| 6,180,123 B1 | 1/2001 | Mondet |
| 6,214,329 B1 | 4/2001 | Brieva et al. |
| 6,227,735 B1 | 5/2001 | Gueret |
| 6,258,916 B1 | 7/2001 | Michaud et al. |
| 6,274,131 B1 | 8/2001 | Piot et al. |
| 6,345,923 B2 | 2/2002 | Gueret |
| 6,372,235 B1 | 4/2002 | Livoreil et al. |
| 6,464,967 B1 | 10/2002 | Collin |
| 6,491,927 B1 | 12/2002 | Arnaud et al. |
| 6,491,931 B1 | 12/2002 | Collin |
| 6,511,655 B1 | 1/2003 | Müller et al. |
| 6,875,245 B2 | 4/2005 | Pavlin |
| 7,288,262 B1 | 10/2007 | Livoreil |
| 2002/0031533 A1 | 3/2002 | Afriat |
| 2002/0098217 A1 | 7/2002 | Piot et al. |
| 2002/0110571 A1 | 8/2002 | Kanji et al. |
| 2002/0127257 A1 | 9/2002 | Gers-Barlag et al. |
| 2002/0131941 A1 | 9/2002 | Habeck et al. |
| 2003/0086951 A9 | 5/2003 | Piot et al. |
| 2004/0071367 A1 | 4/2004 | Irani et al. |

(Continued)

FOREIGN PATENT DOCUMENTS

DE 197 51 221 A1 5/1999

(Continued)

OTHER PUBLICATIONS

Office Action dated Aug. 27, 2008 in co-pending U.S. Appl. No. 10/654,907.
Abstract for Okuyama, M. "Recent Research and Development of Mascara and Eyeliner," Fragrance Journal, 1997, vol. 25, No. 8, pp. 58-64.
Boutevin, B. et al., "Study of Morphological and Mechanical Properties of PP/PBT," Polymer Bulletin, 34, pp. 117-123, (1995).
Co-pending U.S. Appl. No. 10/656,201, filed Sep. 8, 2003.
Co-pending U.S. Appl. No. 11/056,239, filed Feb. 14, 2005.
English language Abstract of EP 1 172 078, dated Jan. 16, 2002.
English language Abstract of FR 2 079 785, dated Nov. 12, 1971.
English language Abstract of FR 2 792 190, dated Oct. 20, 2000.
English language Abstract of FR 2 844 710, dated Mar. 26, 2004.
English language Abstract of FR 2 844 999, dated Apr. 2, 2004.

(Continued)

Primary Examiner — Jyothsna A Venkat
(74) Attorney, Agent, or Firm — Finnegan, Henderson, Farabow, Garrett & Dunner, L.L.P.

(57) ABSTRACT

The disclosure relates to a cosmetic composition comprising, in a cosmetically acceptable medium, a wax having a tack of greater than or equal to 0.7 N.s and a hardness of less than or equal to 3.5 MPa. The wax may be a $C_{20}$-$C_{40}$ alkyl (hydroxystearoyloxy)stearate. The present disclosure also relates to a make-up or care process using the cosmetic composition, and an assembly for packaging and applying a product for coating keratin fibers.

51 Claims, 1 Drawing Sheet

U.S. PATENT DOCUMENTS

| | | | |
|---|---|---|---|
| 2004/0091447 | A1 | 5/2004 | Pays et al. |
| 2004/0096473 | A1 | 5/2004 | Jager-Lezer |
| 2004/0137020 | A1 | 7/2004 | De La Poterie et al. |
| 2004/0137021 | A1 | 7/2004 | De La Poterie et al. |
| 2004/0142831 | A1 | 7/2004 | Jager Lezer |
| 2005/0172421 | A1 | 8/2005 | Jager-Lezer et al. |
| 2005/0188474 | A1 | 9/2005 | De La Poterie et al. |
| 2005/0191258 | A1 | 9/2005 | De La Poterie et al. |
| 2005/0191262 | A1 | 9/2005 | De La Poterie et al. |

FOREIGN PATENT DOCUMENTS

| | | |
|---|---|---|
| DE | 198 17 522 | 10/1999 |
| EP | 0 360 708 | 3/1990 |
| EP | 0 549 494 | 6/1993 |
| EP | 0 611 170 | 8/1994 |
| EP | 0 686 858 | 12/1995 |
| EP | 0 811 336 | 12/1997 |
| EP | 0 811 337 | 12/1997 |
| EP | 0 842 620 | 5/1998 |
| EP | 0 998 905 B1 | 7/1999 |
| EP | 0 951 897 | 10/1999 |
| EP | 0 955 039 | 11/1999 |
| EP | 0 987 002 | 3/2000 |
| EP | 1 068 854 | 1/2001 |
| EP | 1 080 713 A2 | 3/2001 |
| EP | 1 086 945 | 3/2001 |
| EP | 1 157 683 | 11/2001 |
| EP | 1 172 078 | 1/2002 |
| EP | 1 191 041 | 3/2002 |
| EP | 1 201 221 | 5/2002 |
| EP | 0 921 217 | 12/2003 |
| EP | 1 396 257 | 3/2004 |
| EP | 1 396 258 | 3/2004 |
| EP | 1 396 259 | 3/2004 |
| EP | 1 400 234 | 3/2004 |
| EP | 1 424 058 | 6/2004 |
| FR | 2 079 785 | 11/1971 |
| FR | 2 232 303 | 1/1975 |
| FR | 2 607 373 | 6/1988 |
| FR | 2 687 569 | 8/1993 |
| FR | 2 773 063 | 7/1999 |
| FR | 2 792 190 | 10/2000 |
| FR | 2 844 185 | 3/2004 |
| FR | 2 844 710 | 3/2004 |
| FR | 2 844 999 | 4/2004 |
| JP | 6-9341 | 1/1994 |
| JP | 8-506342 | 7/1996 |
| JP | 9-132511 | 5/1997 |
| JP | 11-255619 | 9/1999 |
| JP | 2000-136110 | 5/2000 |
| JP | 2001-48750 | 2/2001 |
| JP | 2001-64156 | 3/2001 |
| JP | 2002-145739 | 5/2002 |
| JP | 2003-95873 | 4/2003 |
| JP | 2003-95875 | 4/2003 |
| WO | WO 91/12793 | 9/1991 |
| WO | WO 93/23008 | 11/1993 |
| WO | WO 94/17775 | 8/1994 |
| WO | WO 98/42298 | 10/1998 |
| WO | WO 01/03653 | 1/2001 |
| WO | WO 01/19333 | 3/2001 |
| WO | WO 02/03931 | 1/2002 |
| WO | WO 02/47031 | 6/2002 |

OTHER PUBLICATIONS

English translation of Notice of Reasons for Rejection mailed May 29, 2007, in the related Japanese Patent Application No. 2005-33677.
European Search Report No. EP 05 29 0253, dated Apr. 28, 2005.
Hamley, I.W., "Crystallization in Block Copolymers," Advances in Polymer Science, vol. 148, pp. 113-137 (1999).
Nojima, S. et al., "Melting Behavior of Poly (e-caprolactone)-block-Polybutadiene Copolymers," Macromolecules, vol. 32, No. 11, pp. 3727-3734 (1999).
Notice of Allowance mailed in co-pending U.S. Appl. No. 11/056,239, dated Jun. 16, 2010.
Office Action mailed Apr. 29, 2009, in co-pending U.S. Appl. No. 11/056,239.
Office Action mailed Aug. 28, 2007, in co-pending U.S. Appl. No. 10/656,201.
Office Action mailed Dec. 11, 2009, in co-pending U.S. Appl. No. 11/056,239.
Office Action mailed Dec. 3, 2008, in co-pending U.S. Appl. No. 10/654,907.
Office Action mailed Feb. 10, 2009, in co-pending U.S. Appl. No. 10/656,201.
Office Action mailed Mar. 31, 2010, in co-pending U.S. Appl. No. 10/656,201.
Office Action mailed May 30, 2008, in co-pending U.S. Appl. No. 10/656,201.
Office Action mailed May 8, 2009, in co-pending U.S. Appl. No. 10/654,907.
Office Action mailed Nov. 9, 2009, in co-pending U.S. Appl. No. 10/654,907.
Okuyama, M. "Recent Research and Development of Mascara and Eyeliner," Fragrance Journal, 1997, vol. 25, No. 8, pp. 58-64.
Pigeon, R. et al., "Chimie Macromoleculaire Appliquee, ", vol. 40/41, No. 600, pp. 139-158 (1974).
Prince, L.M., "Microemulsions Theory and Practice," Academic Press, 1977, pp. 21-32.
Rangarajan P., et al., "Morphology of Semi-Crystalline Block Copolymers of Ethylene- (ethylene-alt-propylene)," Macromolecules, 26, 4640-4645 (1993).
Richter, P. et al., "Polymer Aggregates with Crystalline Cores: The System Poly(ethylene)-poly(ethylene-propylene)," Macromolecules, 30, 1053-1068 (1997).
Summary of Pigeon, R. et al., "Chim Macromoléclaire Appliquée, ", vol. 40/41, No. 600, pp. 139-158 (1974).
Terech, P., "Low-Molecular Weight Organogelators," Specialist Surfactants, Chapter 8, 1997, pp. 209-263.
Encyclopedia of Chem. Tech. "Sulfonation and Sulfation to Thorium and Thorium Compounds", Third Edition, vol. 22, John Wiley & Sons., Jan. 1983.
Co-pending U.S. Appl. No. 10/654,907 filed Sep. 5, 2003.
French Search Report for FR 0 211 096 (French priority application for copending Application No. 10/654,907), dated May 19, 2003.
English language Derwent Abstract of JP 2003-95873., Apr. 2003.
English language Derwent Abstract of JP 2003-95875, Apr. 2003.
French Search Report dated Apr. 28, 2003.
Derwent Abstract for DE 197 51 221, May 1999.
Derwent Abstract for EP 1 080 713, Mar. 2001.
Office Action dated Feb. 26, 2008 in co-pending U.S. Appl. No. 10/654,907 filed Sep. 5, 2003.
English language Derwent Abstract for JP H06-9341, May 1997.
English language Derwent Abstract for JP H09-132511, May 1997.

* cited by examiner

COMPOSITION FOR COATING KERATIN FIBRES COMPRISING A TACKY WAX

This application claims benefit of U.S. Provisional Application No. 60/412,854, filed Sep. 24, 2002; U.S. Provisional Application No. 60/418,345, filed Oct. 16, 2002; U.S. Provisional Application No. 60/418,357, filed Oct. 16, 2002; U.S. Provisional Application No. 60/412,853, filed Sep. 24, 2002; and U.S. Provisional Application No. 60/412,855, filed Sep. 24, 2002.

Disclosed herein is a cosmetic composition for coating keratin fibres, comprising at least one tacky wax. Also disclosed herein is a cosmetic product for making up or treating keratin fibres such as the eyelashes, the eyebrows and the hair.

Further disclosed herein is a care or makeup composition for the eyes, such as an eyeliner or an eyeshadow.

The cosmetic composition disclosed herein may be a makeup composition, such as a mascara, a makeup base for keratin fibres, a base coat, a composition to be applied onto a makeup, also known as a top coat, or a composition for treating keratin fibres. Mention may be made of the composition as a mascara.

The term "mascara" is understood as meaning a composition intended to be applied to the eyelashes: it can be a makeup composition for the eyelashes, a makeup base for the eyelashes, a composition to be applied onto a mascara, also known as a top coat, or a cosmetic treatment composition for the eyelashes. Mascara may be used for the eyelashes of human beings, as well as false eyelashes.

Mascaras are commonly prepared according to two types of formulations: water-based mascaras, known as cream mascaras, in the form of an emulsion of waxes in water, and anhydrous mascaras or mascaras with a low water content, known as waterproof mascaras, in the form of dispersions of waxes in organic solvents.

It is known practice to use various waxes to formulate mascaras, for instance those described in document WO-A-91/12793, for example beeswax, candelilla wax, carnauba wax or polyethylene wax.

However, when mascaras comprise certain waxes, for instance carnauba wax, rice bran wax or polyethylene wax, the makeup of the eyelashes obtained can look grainy, with a non-smooth and non-uniform makeup result, which may render the makeup result unattractive.

Moreover, to obtain a mascara with good charging properties, i.e. to obtain heavy makeup of the eyelashes, it is possible to incorporate into the mascara at least one wax in a total amount of greater than 25% by weight, relative to the total weight of the mascara. However, when using conventional waxes such as beeswax, candelilla wax, and carnauba wax at a high amount, the mascara composition can acquire a very thick consistency, or even become too compact, and thus may not be applied easily to the eyelashes with the mascara brush applicators commonly used. The excessively thick mascara may be deposited on the eyelashes in the form of lumps and the makeup result thus obtained may not have the desired smooth appearance; the makeup result may not be uniform and may look unattractive.

In addition, certain waxes such as orange wax or lanolin wax, used at amounts of greater than 25% by weight, may produce compositions that are not sufficiently stable, for instance after storage for two weeks at room temperature (25° C.): the composition may set to a solid (substantial increase in viscosity) or undergo a phase separation that may be seen with the naked eye. In such instances, the composition is then unsuitable for application to the eyelashes.

Also disclosed herein is a cosmetic composition for coating keratin fibres, wherein the cosmetic composition makes it possible to obtain a smooth, uniform makeup of the keratin fibres.

Further disclosed herein is a cosmetic composition for coating keratin fibres, for example the eyelashes, that may be applied easily to the keratin fibers, may make it possible to obtain rapidly the expected makeup, may comprise a high content of wax, and that may have good charging properties on the eyelashes.

Still further disclosed herein is a cosmetic composition for coating keratin fibres, which can remain stable, especially after storage for 24 hours at 25° C.

It has been discovered that such a composition may be obtained by using at least one wax that has tacky properties (high tack). Such waxes can produce a composition for coating keratin fibres, for instance mascara, that can be applied easily to the eyelashes, show good attachment to the eyelashes, make it possible to obtain the expected makeup rapidly, and thus can lead to the formation of a smooth, uniform makeup result that does not look grainy.

Furthermore, the at least one tacky wax may be incorporated into the composition in an amount that may be up to 60% by weight, relative to the total weight of the composition, without the composition setting to a solid: the composition can remain stable (such as after 24 hours at 25° C.), retain a creamy consistency and apply easily to the eyelashes.

Furthermore, such a mascara as disclosed herein can provide good separation of the eyelashes in that they do not stick together.

Another aspect disclosed herein is a cosmetic composition for coating keratin fibres comprising, in a cosmetically acceptable medium, at least one wax having a tack of greater than or equal to 0.7 N.s and a hardness of less than or equal to 3.5 MPa.

Yet another aspect disclosed herein is a non-therapeutic cosmetic makeup or care process for keratin fibres, such as the eyelashes, comprising applying to keratin fibres a composition as defined above.

Still another aspect disclosed herein is a method for obtaining a makeup result on keratin fibers that can be, as desired, uniform, and/or smooth, and/or heavy, and/or impart good separation of the made-up keratin fibres, comprising applying to keratin fibers a cosmetic composition as defined above.

Yet still another aspect disclosed herein is the use of at least one wax having a tack of greater than or equal to 0.7 N.s and a hardness of less than or equal to 3.5 MPa, in a mascara composition, to obtain a uniform and/or smooth and/or heavy makeup result on eyelashes and/or to obtain a stable mascara and/or good separation of the made-up eyelashes.

In the case of eyeshadows or eyeliners, one may seek to obtain, in addition to stability, a glossy composition which is easily applied to the skin, which forms a smooth and uniform film and which does not shrink during application and adheres to the skin following application. A composition such as this can be obtained by using the at least one tacky wax mentioned above.

Accordingly, further disclosed herein is a care or makeup composition for the eye area, such as an eyeliner or an eyeshadow, comprising, in a cosmetically acceptable medium, at least one wax having a tack of greater than or equal to 0.7 N.s and a hardness of less than or equal to 3.5 MPa.

Another aspect disclosed herein is a non-therapeutic cosmetic makeup or care process for the eye area, comprising the application, to the contour of the eye, the lower or upper edge of the eye or the eyelid, of a composition as defined above.

Figure 1:
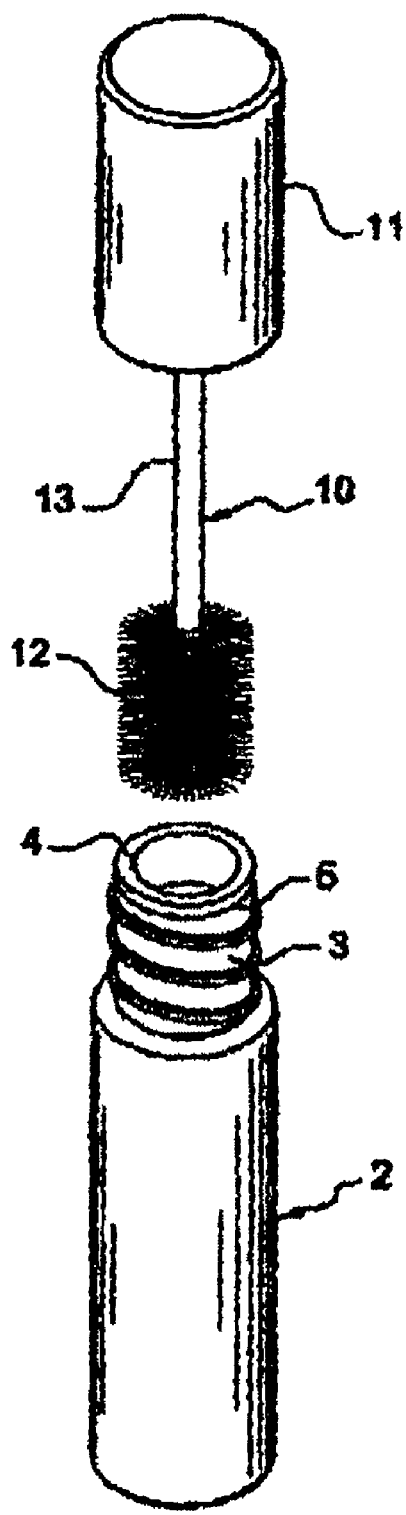
FIG. 1 shows one embodiment of a packaging and applicator assembly comprising a composition for coating keratin fibres as disclosed herein.

The term "cosmetically acceptable medium" means a cosmetic medium that is compatible with the eyelashes or the skin.

The at least one wax, also known as the at least one tacky wax, as disclosed herein, has a tack of greater than or equal to 0.7 N.s, for example, ranging from 0.7 N.s to 30 N.s, such as greater than or equal to 1 N.s, for example ranging from 1 N.s to 20 N.s and such as greater than or equal to 2 N.s, for example, ranging from 2 N.s to 10 N.s and, for instance, ranging from 2 N.s to 5 N.s.

The at least one tacky wax has a hardness of less than or equal to 3.5 MPa, for example, ranging from 0.01 to 3.5 MPa, for instance, ranging from 0.05 MPa to 3 MPa, and for further example, ranging from 0.1 MPa to 2.5 MPa.

For the purposes of the present disclosure, the term "wax" means a lipophilic fatty compound that is solid at room temperature (25° C.) and atmospheric pressure (760 mmHg, i.e. $10^5$ Pa), with a reversible solid/liquid change of state, having a melting point of greater than 30° C., such as greater than 55° C., which may be up to 200° C., for instance up to 120° C.

By bringing the wax to its melting point, it is possible to make it miscible with oils and to form a microscopically homogeneous mixture. Further, on cooling the mixture to room temperature, recrystallization of the wax in the oils of the mixture is obtained.

The melting point values correspond, as disclosed herein, to the melting peak measured using a differential scanning calorimeter (D.S.C.), for example the calorimeter sold under the name DSC 30 by the company Mettler, with a temperature rise of 5 or 10° C. per minute.

The tack of the at least one wax is measured at 20° C. using the texturometer sold under the name TA-XT2i by the company Rheo, equipped with an acrylic polymer rotor in the form of a cone forming an angle of 45°, by measuring the change in force (compression force or stretching force) (F) as a function of time, during the following operation: The rotor is displaced at a speed of 0.5 mm/s and then penetrates into the wax to a penetration depth of 2 mm. When the rotor has penetrated the wax to a depth of 2 mm, the rotor is held stationary for 1 second (corresponding to the relaxation time) and is then withdrawn at a speed of 0.5 mm/s. During the relaxation time, the force (compression force) decreases greatly until it becomes zero, and then, during the withdrawal of the rotor, the force (stretching force) becomes negative before rising again to the value 0. Tack corresponds to the integral of the curve of the force as a function of time for the portion of the curve corresponding to the negative force values (stretching force). The tack value is expressed in N.s.

To perform the tack measurement of the at least one wax, the wax is melted at a temperature equal to the melting point of the wax+10° C. The molten wax is cast in a container 25 mm in diameter and 20 mm deep. The wax is recrystallized at room temperature (25° C.) for 24 hours such that the surface of the wax is flat and smooth, and the wax is then kept for at least 1 hour at 20° C. before performing the tack measurement.

The hardness of the at least one wax is determined by measuring the compression force, which is measured at 20° C. using the texturometer sold under the name TA-XT2i by the company Rheo, equipped with a stainless-steel cylinder 2 mm in diameter travelling at a measuring speed of 0.1 mm/s, and penetrating the wax to a penetration depth of 0.3 mm. To perform the hardness measurement, the wax is melted at a temperature equal to the melting point of the wax+20° C. The molten wax is cast in a container 30 mm in diameter and 20 mm deep. The wax is recrystallized at room temperature (25° C.) for 24 hours and is then kept for at least 1 hour at 20° C. before performing the hardness measurement. The hardness value is the compression force measured divided by the area of the texturometer cylinder in contact with the wax.

Tacky waxes that may be used include the $C_{20}$-$C_{40}$ alkyl (hydroxystearoyloxy)stearate (the alkyl group containing from 20 to 40 carbon atoms), alone or as a mixture, such as a $C_{20}$-$C_{40}$ alkyl 12-(12'-hydroxystearoyloxy)stearate, chosen from compounds of formula (I):

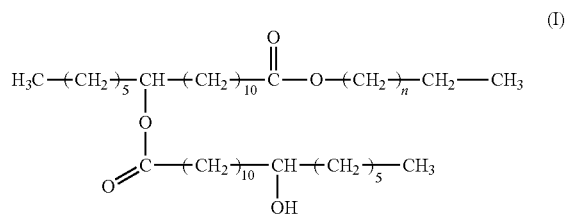

or a mixture of compounds of formula (I), wherein n is an integer ranging from 18 to 38.

Thus, another aspect disclosed herein is a composition for coating keratin fibres, for instance a mascara, comprising, in a cosmetically acceptable medium, a $C_{20}$-$C_{40}$ alkyl (hydroxystearoyloxy)stearate (mention may be made of $C_{20}$-$C_{40}$ alkyl 12-(12'-hydroxystearoyloxy)stearate), such as those described in formula (I).

Mention may be made of tacky wax that is sold under the names "Kester Wax K 82 P" and "Kester Wax K 80 P" by the company Koster Keunen.

The at least one wax may be in the form of an aqueous microdispersion of wax particles. The expression "aqueous microdispersion of wax" as disclosed herein means an aqueous dispersion of wax particles in which the size of the said wax particles is less than or equal to about 1 μm. Wax microdispersions are stable dispersions of colloidal wax particles, and are described in *Microemulsions Theory and Practice*, L. M. Prince Ed., Academic Press (1977) pages 21-32.

In obtaining these wax microdispersions, mention may be made of melting the wax in the presence of a surfactant, and optionally of a portion of water, followed by gradual addition of hot water with stirring. The intermediate formation of an emulsion of the water-in-oil type may be observed, followed by a phase inversion, with final production of a microemulsion of the oil-in-water type. On cooling, a stable microdispersion of solid wax colloidal particles can be obtained.

The wax microdispersions may also be obtained by stirring the mixture of wax, surfactant and water using stirring means such as ultrasound, a high-pressure homogenizer, or turbomixers.

The particles of the wax microdispersion may have mean sizes of less than 1 μm (for example, ranging from 0.02 μm to 0.99 μm) such as less than 0.5 μm (for further example, ranging from 0.06 μm to 0.5 μm). These particles may comprise mainly a wax or a mixture of waxes. However, they may comprise a small proportion of oily and/or pasty fatty additives, a surfactant and/or a common liposoluble additive/active agent.

The at least one tacky wax may be present in the composition as disclosed herein in an amount ranging from 0.5% to 60% by weight, such as an amount greater than or equal to 0.5% and less than 25% by weight, for instance, ranging from 5% to 50% by weight, for further instance, ranging from 10 to 40% by weight, relative to the total weight of the composition. In addition, the at least one tacky wax may be present in the composition as disclosed herein in an amount greater than 25% by weight relative to the total weight of the composition, for example ranging from 25% to 60% by weight, such as greater than 27% by weight, for further example from 27% to 50% by weight, such as greater than 28% by weight, for still further example from 28% to 45% by weight, such as greater than 30% by weight, for instance, from 30% to 40% by weight.

Second Wax

In yet another aspect as disclosed herein, the composition can comprise at least one additional wax, also known as the at least one hard wax, which has a hardness of greater than or equal to 6 MPa, for example, ranging from 6 MPa to 30 MPa, such as greater than or equal to 7 MPa, for further example ranging from 7 MPa to 25 MPa, such as greater than or equal to 8 MPa, for even further example ranging from 8 to 25 MPa, such as greater than or equal to 9 MPa, for instance from 9 to 20 Mpa.

The hardness of the at least one hard wax is measured according to the same protocol described above for the at least one tacky wax.

Hard waxes that may be used include carnauba wax, candelilla wax, polyethylene waxes, hydrogenated jojoba oil, sumach wax, ceresin, octacosanyl stearate, tetracontanyl stearate, shellac wax, behenyl fumarate, bis(1,1,1-trimethylolpropane) tetrastearate sold under the name "Hest 2T-4S" by the company Heterene, bis(1,1,1-trimethylolpropane) tetrabehenate sold under the name Hest 2T-4B by the company Heterene, ozokerites, for instance the product sold under the name "Ozokerite Wax SP 1020 P" by the company Strahl & Pitsch, and the wax obtained by hydrogenation of olive oil esterified with stearyl alcohol, sold under the name Phytowax Olive 18 L 57 by the company Sophim.

The at least one hard wax may be in the form of an aqueous microdispersion of wax particles as described for the at least one tacky wax.

The at least one hard wax may be present in the composition as disclosed herein in an amount ranging from 0.1% to 30% by weight, for example, ranging from 1% to 20% by weight and for further example ranging from 2% to 10% by weight, relative to the total weight of the composition.

For certain cosmetic applications, it may be desirable to be able to reduce the natural tack of the at least one tacky wax, for instance when it is present in large amounts (typically greater than 10%, such as 20% or 25%) while conserving the beneficial properties of a smooth and uniform deposit. Thus, in the case of formulations of mascara type, certain users seek to perfectly individualize the eyelashes, which is not always optimal in the presence of a tacky wax.

It has been found, unexpectedly, that it is possible to satisfy this additional requirement, with the proviso that the at least one tacky wax is combined with at least one compound chosen from dextrin esters of fatty acids and/or at least one filler having a BET specific surface area of greater than or equal to 100 m²/g.

Mention may be made of the composition as disclosed herein comprising at least one compound chosen from dextrin esters of fatty acids and/or at least one filler having a BET specific surface area of greater than or equal to 100 m2/g.

Filler with a Specific Surface Area

The fillers may have a specific surface area of greater than or equal to 100 m²/g, for example, ranging from 100 to 5 000 m²/g, for further example ranging from 150 to 1 000 m²/g, or such as from 200 to 800 m²/g.

The term "fillers" denotes particles of any shape, which are insoluble in the medium of the composition, irrespective of the temperature at which the composition is manufactured.

The expression "fillers with a specific surface area" means fillers having a specific surface area measured according to the BET method of greater than or equal to 100 m²/g. The "BET specific surface area" is determined according to the BET (Brunauer-Emmet-Teller) method described in "The Journal of the American Chemical Society", vol. 60, page 309, February 1938, and corresponding to international standard ISO 5794/1 (appendix D). The BET specific surface area corresponds to the total specific surface area (i.e. micropores included) of the filler.

The amount of filler in the composition as disclosed is generally adjusted so as to control the tack of the at least one wax to the desired value. Thus, the fillers in accordance the disclosure can be useful for preparing cosmetic compositions comprising at least 10%, for example 20%, such as at least 25% and for instance 27% by weight of at least one tacky wax.

By way of illustration, fillers may be present in the composition as disclosed herein in an amount ranging from 0.1% to 25%, for example, from 0.5% to 20% such as from 1% to 15% by weight relative to the total weight of the composition.

Mention may be made of the at least one wax (tacky wax) and fillers with a specific surface area being present in an amount such that the weight ratio of the at least one wax relative to the fillers with a specific surface area ranges from 350 to 0.1, for example from 100 to 0.5, such as from 50 to 0.8, and for further example, from 30 to 1.

The particles that compose the fillers with a specific surface area may have a mean size ranging from 0.01 to 100 μm, for instance from 0.1 to 50 μm, such as from 1 to 20 μm. The term "mean size" denotes the size given by the statistical particle size distribution to half of the population, noted as D50.

The fillers with a specific surface area as disclosed herein may be chosen from organic fillers, mineral fillers and mixtures thereof.

The organic fillers may be chosen from polyolefinic waxes, for instance polyethylene waxes such as those sold under the name "Performalen 2000®" by the company New Phase Technology, and from polymeric fillers such as polymethyl methacrylate (PMMA), for instance Jurymer MB1® sold by Nihon Junyaku or polytetrafluoroethylene (PTFE). Non-limiting illustrations of mineral fillers that may be mentioned include silicas, silicates, aluminas and aluminosilicates, for example, those sold under the name "Sunsil 130®" by the company Sunjin Chemical or "Silica Beads SB 150®" by the company Miyoshi.

The particles that comprise the fillers with a specific surface area may have varied shapes. For example, these particles may be globular, lamellar, spherical, hollow or solid. Mention may be made of hollow fillers.

Thus, in the case of mineral fillers, mention may be made of hollow silica microspheres, such as "Sunsphere H-51" from Asahi Glass, with a specific surface area equal to 770 m²/g, and "Sunsil 130" from Sunjin Chemical, with a specific surface area of 200-260 m²/g.

According to one aspect of the disclosure, the composition comprises at least one wax (tacky wax) and at least one filler with a specific surface area of greater than or equal to 100 m²/g, such as hollow, spherical silica, hollow silica microspheres and/or polyethylene wax.

Dextrin Ester of Fatty Acid(s)

Of the dextrin esters of fatty acids that may be combined with the at least one tacky wax in the composition as disclosed herein, mention may be made of those chosen from dextrin monoesters and polyesters of at least one fatty acid, for example, those corresponding to the formula (II):

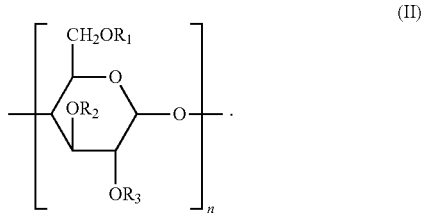

(II)

wherein:
- n is an integer ranging from 3 to 200, for example ranging from 20 to 150, such as ranging from 25 to 50,
- the radicals $R_1$, $R_2$ and $R_3$, which may be identical or different, are chosen from hydrogen and acyl groups (R—CO—) wherein the acyl radical R is chosen from linear, branched, saturated and unsaturated hydrocarbon-based groups comprising from 6 to 50 carbon atoms, for example from 7 to 29, for further example from 7 to 21, such as from 11 to 19, for even further example, from 13 to 17, or even 15, carbon atoms, provided that at least one of the said radicals $R_1$, $R_2$ or $R_3$ is not hydrogen.

For example, $R_1$, $R_2$ and $R_3$ may be chosen from hydrogen and acyl groups (R—CO—) wherein the acyl radical R is a hydrocarbon-based radical as defined above, provided that at least two of the said radicals $R_1$, $R_2$ or $R_3$ are identical and are not hydrogen.

The radicals $R_1$, $R_2$ and $R_3$ may all comprise an acyl group (R—CO), which is identical or different. According to one aspect, they are identical.

For instance, n may range from 25 to 50, and for example, may be equal to 38 in the formula (II) of the ester as disclosed herein.

When the radicals $R_1$, $R_2$ and $R_3$, which may be identical or different, comprise an acyl group (R—CO), mention may be made of acyl radicals chosen from caprylyl, caproyl, lauroyl, myristyl, palmityl, stearyl, eicosanyl, docosanoyl, isovaleryl, ethyl-2 butyryl, ethylmethylacetyl, isoheptanyl, ethyl-2 hexanyl, isononanyl, isodecanyl, isotridecanyl, isomyristyl, isopalmityl, isostearyl, isohexanyl, decenyl, dodecenyl, tetradecenyl, myristyl, hexadecenoyl, palmitoleyl, oleyl, elaidyl, eicosenyl, sorbyl, linoleyl, linolenyl, punicyl, arachidonyl, stearolyl radicals, and mixtures thereof.

Mention may be made of at least one dextrin palmitate being used as a dextrin ester of fatty acids. This ester may be used alone or as a mixture with other esters.

The dextrin esters of fatty acids may have a degree of substitution of less than or equal to 2.5, on the basis of one glucose unit, for example ranging from 1.5 to 2.5, such as from 2 to 2.5, on the basis of one glucose unit. The weight-average molecular weight of the dextrin esters may be from 10 000 to 150 000, for instance, from 12 000 to 100 000, such as from 15 000 to 80 000.

Dextrin esters of fatty acids, such as dextrin palmitates, are commercially available under the name Rheopearl TL or Rheopearl KL by the company Chiba Flour.

The dextrin esters of fatty acids may be present in the composition as disclosed herein in an amount ranging from 0.1% to 20%, for example, from 0.5% to 15% by weight and for further example from 1% to 10% by weight, relative to the total weight of the composition.

Mention may be made of the at least one wax (tacky wax) and the at least one compound chosen from dextrin esters of fatty acids, present in an amount such that the weight ratio of the at least one wax relative to the at least one compound chosen from dextrin esters ranges from 350 to 0.1, for example from 100 to 0.5 and such as from 50 to 1, or even from 15 to 2.

Cosmetically Acceptable Medium

The physiologically acceptable medium of the composition may comprise a volatile solvent chosen from water, volatile organic solvents, volatile oils, and mixtures thereof.

The composition as disclosed herein may comprise an aqueous medium, comprising an aqueous phase, which may form the continuous phase of the composition.

The aqueous phase may be comprised mainly of water. It may also comprise a mixture of water and of water-miscible solvent (water miscibility of greater than 50% by weight at 25° C.), for instance lower monoalcohols comprising from 1 to 5 carbon atoms, such as ethanol or isopropanol, glycols comprising from 2 to 8 carbon atoms, such as propylene glycol, ethylene glycol, 1,3-butylene glycol, dipropylene glycol, $C_3$-$C_4$ ketones, and $C_2$-$C_4$ aldehydes.

The aqueous phase (water and optionally the water-miscible organic solvent) may be present in an amount ranging from 1% to 95% by weight, relative to the total weight of the composition, for example ranging from 3% to 80% by weight, such as ranging from 5% to 60% by weight, relative to the total weight of the composition.

The composition as disclosed herein may also comprise an oil or organic solvent that may form a fatty phase, for example a continuous fatty phase. The composition may be an anhydrous composition.

For the purposes of the disclosure, the expression "volatile oil or organic solvent" means any non-aqueous medium that can evaporate on contact with the keratin fibre in less than one hour at room temperature and atmospheric pressure. The volatile organic solvent) and volatile oils as disclosed herein are volatile cosmetic organic solvents and oils, that are liquid at room temperature, having a non-zero vapour pressure at room temperature and atmospheric pressure, ranging from 0.13 Pa to 40 000 Pa ($10^{-3}$ to 300 mmHg), for instance ranging from 1.3 Pa to 13 000 Pa (0.01 to 100 mmHg) and such as ranging from 1.3 Pa to 1 300 Pa (0.01 to 10 mmHg). The expression "non-volatile oil" means an oil which remains on the keratin fibre at room temperature and atmospheric pressure for at least several hours and which has a vapour pressure of less than $10^{-3}$ mmHg (1.33 Pa).

These oils may be hydrocarbon-based oils, silicone oils, or mixtures thereof.

The expression "hydrocarbon-based oil" means an oil mainly comprising hydrogen and carbon atoms and optionally at least one of oxygen, nitrogen, sulphur or phosphorus atoms. The volatile hydrocarbon-based oils may be chosen from hydrocarbon-based oils comprising from 8 to 16 carbon atoms, for example $C_8$-$C_{16}$ branched alkanes, for instance $C_8$-$C_{16}$ isoalkanes of petroleum origin (also known as isoparaffins), for instance isododecane (also known as 2,2,4,4,6-pentamethylheptane), isodecane and isohexadecane, and, for example, the oils sold under the trade names Isopars or Permetyls, $C_8$-$C_{16}$ branched esters, isohexyl neopentanoate, and mixtures thereof. Other volatile hydrocarbon-based oils, for instance petroleum distillates, such as those sold under the name Shell Solt by the company Shell, may also be used. Mention may be made of the volatile solvent chosen from hydrocarbon-based volatile oils comprising from 8 to 16 carbon atoms, and mixtures thereof.

Volatile oils which may also be used are volatile silicones, such as linear or cyclic volatile silicone oils, for example, those with a viscosity $\leq 8$ centistokes ($8\times10^{-6}$ m$^2$/s) and especially comprising from 2 to 10 silicon atoms, these silicones optionally comprising alkyl or alkoxy groups comprising from 1 to 22 carbon atoms. Regarding volatile silicone oils that may be used in the invention, mention may be made of octamethylcyclotetrasiloxane, decamethylcyclopentasiloxane, dodecamethylcyclohexasiloxane, heptamethylhexyltrisiloxane, heptamethyloctyltrisiloxane, hexamethyidisiloxane, octamethyltrisiloxane, decamethyltetrasiloxane and dodecamethylpentasiloxane, and mixtures thereof.

The volatile oil may be present in the composition as disclosed in an amount ranging from 0% to 98% by weight, relative to the total weight of the composition, for instance from 0% to 65% by weight.

The composition can also comprise at least one non-volatile oil chosen from non-volatile hydrocarbon-based oils and silicone oils.

Non-volatile hydrocarbon-based oils which may be mentioned are:

hydrocarbon-based plant oils such as triglycerides comprised of fatty acid esters and of glycerol wherein the fatty acids may have varied chain lengths from $C_4$ to $C_{24}$, these chains may be linear or branched, and saturated or unsaturated; these oils are, for example, wheat germ oil, sunflower oil, grape seed oil, sesame oil, corn oil, apricot oil, castor oil, karite butter, avocado oil, olive oil, soybean oil, sweet almond oil, palm oil, rapeseed oil, cotton oil, hazelnut oil, macadamia oil, jojoba oil, alfalfa oil, poppy oil, pumpkin oil, marrow oil, blackcurrant seed oil, evening primrose oil, millet oil, barley oil, quinoa oil, rye oil, safflower oil, candlenut oil, passion flower oil and musk rose oil; or alternatively caprylic/capric acid triglycerides such as those sold by Stearineries Dubois or those sold under the names Miglyol 810, 812 and 818 by Dynamit Nobel;

synthetic ethers comprising from 10 to 40 carbon atoms;

linear or branched hydrocarbons of mineral or synthetic origin, such as petroleum jelly, polydecenes, hydrogenated polyisobutene such as parleam, and squalane, and mixtures thereof;

synthetic esters such as oils of formula $R_1COOR_2$ wherein $R_1$ represents a linear or branched fatty acid residue comprising from 1 to 40 carbon atoms and $R_2$ is chosen from branched hydrocarbon-based chains comprising from 1 to 40 carbon atoms, provided that $R_5+R_6 \geq 10$, such as, for example, purcellin oil (cetostearyl octanoate), isopropyl myristate, isopropyl palmitate, $C_{12}$-$C_{15}$ alkyl benzoate, hexyl laurate, diisopropyl adipate, isononyl isononanoate, 2-ethylhexyl palmitate, isostearyl isostearate, alkyl or polyalkyl octanoates, decanoates or ricinoleates such as propylene glycol dioctanoate; hydroxylated esters such as isostearyl lactate and diisostearyl malate; and pentaerythritol esters;

fatty alcohols that are liquid at room temperature, comprising a branched and/or unsaturated carbon-based chain comprising from 12 to 26 carbon atoms, for instance octyldodecanol, isostearyl alcohol, oleyl alcohol, 2-hexyldecanol, 2-butyloctanol or 2-undecylpentadecanol;

higher fatty acids such as oleic acid, linoleic acid, linolenic acid;

and mixtures thereof.

The non-volatile silicone oils which may be used in the composition as disclosed herein may be non-volatile polydimethylsiloxanes (PDMSs), polydimethylsiloxanes comprising alkyl or alkoxy groups, that are pendent and/or at the end of a silicone chain, the groups each comprising from 2 to 24 carbon atoms, phenylsilicones, for instance phenyltrimethicones, phenyldimethicones, phenyltrimethylsiloxydiphenylsiloxanes, diphenyldimethicones, diphenylmethyldiphenyltrisiloxanes and 2-phenylethyl trimethylsiloxysilicates.

The non-volatile oils may be present in the composition as disclosed herein in an amount ranging from 0 to 30% (such as from 0.1% to 30%) by weight, for example from 0 to 20% by weight (such as 0.1% to 20%) and for further example from 0 to 10% by weight (such as 0.1% to 10%), relative to the total weight of the composition.

The composition as disclosed herein may also further comprise at least one additional wax other than the at least one wax (tacky wax) and the at least one hard wax described above.

The at least one additional wax may be chosen, for example, from beeswax, paraffin waxes, hydrogenated castor oil and silicone waxes. The at least one additional wax may be present in the form of a wax microdispersion as described above for the tacky and hard waxes.

The at least one additional wax may be present in the composition as disclosed herein in an amount ranging from 0.1% to 50% by weight, relative to the total weight of the composition, for example from 0.5% to 30% by weight, such as from 1% to 20% by weight.

The total content of waxes (first wax and/or second wax and/or additional wax) in the composition as disclosed herein may range from 0.7% to 70% by weight, for instance from 5% to 65% by weight, such as from 10% to 60% by weight, and for further instance from 10% to 60% by weight, relative to the total weight of the composition.

The composition as disclosed herein may comprise at least one fatty compound that is pasty at room temperature. For the purposes of this disclosure, the expression "pasty fatty substance" means fatty substances with a melting point ranging from 20 to 55° C., for example 25 to 45° C., and/or a viscosity at 40° C. ranging from 0.1 to 40 Pa·s (1 to 400 poises), such as 0.5 to 25 Pa·s, measured using a Contraves TV or Rheomat 80 viscometer, equipped with a spindle rotating at 60 Hz. A person of ordinary skill in the art can select the spindle for measuring the viscosity from the spindles MS-r3 and MS-r4, on the basis of his general knowledge, so as to be able to carry out the measurement of the pasty compound tested.

These fatty substances are may be hydrocarbon-based compounds, optionally of polymeric type; they can also be chosen from silicone compounds; they may also be in the form of a mixture of hydrocarbon-based compounds and/or silicone compounds. In the case of a mixture of different pasty fatty substances, the hydrocarbon-based pasty compounds (comprising mainly hydrogen and carbon atoms and optionally ester groups) may be used in major proportion.

Among the pasty compounds which may be used in the composition as disclosed herein, non-limiting mention may be made of lanolins and lanolin derivatives such as acetylated lanolins, oxypropylenated lanolins, and isopropyl lanolate, having a viscosity of from 18 to 21 Pa·s, for example 19 to 20.5 Pa·s, and/or a melting point of from 30 to 55° C., and mixtures thereof. It is also possible to use esters of fatty acids or of fatty alcohols, for instance those comprising from 20 to 65 carbon atoms (melting point of about from 20 to 35° C. and/or viscosity at 40° C. ranging from 0.1 to 40 Pa·s), such as triisostearyl or cetyl citrate; arachidyl propionate; polyvinyl laurate; cholesterol esters, such as triglycerides of plant origin, such as hydrogenated plant oils, viscous polyesters such as poly(12-hydroxystearic acid), and mixtures thereof.

Mention may also be made of pasty silicone fatty substances such as polydimethylsiloxanes (PDMSs) comprising pendent chains of the alkyl or alkoxy type comprising from 8 to 24 carbon atoms, and having a melting point of 20-55° C., such as stearyldimethicones, for instance those sold by Dow Corning under the trade names DC2503 and DC25514, and mixtures thereof.

The pasty fatty substance may be present in the composition as disclosed herein in an amount ranging from 0% to 60% by weight, relative to the total weight of the composition, for example, in a proportion of from 0.5% to 45% by weight, and for further example ranging from 2% to 30% by weight, in the composition.

The composition as disclosed herein can contain emulsifying surfactants, which may be present, for example, in a proportion ranging from 2% to 30% by weight relative to the total weight of the composition, such as from 5% to 15%. These surfactants may be chosen from anionic and nonionic surfactants. Reference may be made to the document "Encyclopedia of Chemical Technology, Kirk-Othmer", volume 22, pp. 333-432, 3rd edition, 1979, Wiley, for the definition of the properties and functions (emulsifying) of surfactants, for example pp. 347-377 of the said reference, for the anionic and nonionic surfactants.

Non-limiting mention may be made of the following surfactants that may be used in the composition as disclosed:

nonionic surfactants: fatty acids, fatty alcohols, polyethoxylated or polyglycerolated fatty alcohols such as polyethoxylated stearyl or cetylstearyl alcohol, fatty acid esters of sucrose, alkylglucose esters, such as polyoxyethylenated fatty esters of $C_1$-$C_6$ alkyl glucose, and mixtures thereof;

anionic surfactants: $C_{16}$-$C_{30}$ fatty acids neutralized with amines, aqueous ammonia, alkaline salts, and mixtures thereof.

Mention may also be made of the use of surfactants which make it possible to obtain an oil-in-water or wax-in-water emulsion.

The composition as disclosed herein can comprise at least one film-forming polymer.

The film-forming polymer may be present in the composition as disclosed herein in a solids content ranging from 0.1% to 60% by weight relative to the total weight of the composition, for instance, from 0.5% to 40% by weight, such as from 1% to 30% by weight.

In the present disclosure, the expression "film-forming polymer" means a polymer which is capable, by itself or in the presence of an auxiliary film-forming agent, of forming a continuous and adherent film on a support, for example on keratin materials such as the eyelashes.

Among the film-forming polymers which may be used in the composition of the present invention, suitable non-limiting examples include synthetic polymers, of radical-mediated type or of polycondensate type, polymers of natural origin, and mixtures thereof.

The expression "radical-mediated film-forming polymer" means a polymer obtained by polymerization of monomers containing unsaturation, for example ethylenic unsaturation, each monomer being capable of homopolymerizing (unlike polycondensates).

The film-forming polymers of radical-mediated type may be, for instance, vinyl polymers or copolymers, such as acrylic polymers. The vinyl film-forming polymers can result from the polymerization of monomers containing ethylenic unsaturation and comprising at least one acidic group and/or esters of these acidic monomers and/or amides of these acidic monomers.

Monomers bearing an acidic group which may be used are α,β-ethylenic unsaturated carboxylic acids such as acrylic acid, methacrylic acid, crotonic acid, maleic acid or itaconic acid. Mention may be made of the use of (Meth)acrylic acid and crotonic acid.

The esters of acidic monomers may be chosen from (meth) acrylic acid esters (also known as (meth)acrylates), for example (meth)acrylates of an alkyl, for instance of a $C_1$-$C_{30}$ and $C_1$-$C_{20}$ alkyl, (meth)acrylates of an aryl, for instance of a $C_6$-$C_{10}$ aryl, and (meth)acrylates of a hydroxyalkyl, for instance of a $C_2$-$C_6$ hydroxyalkyl.

Among the alkyl (meth)acrylates, suitable non-limiting mention may be made of methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl (meth)acrylates non-limiting mention may be made of hydroxyethyl acrylate, 2-hydroxypropyl acrylate, hydroxyethyl methacrylate and 2-hydroxypropyl methacrylate.

Among the aryl (meth)acrylates non-limiting mention may be made of benzyl acrylate and phenyl acrylate.

According to one aspect of the disclosure, alkyl (meth) acrylates are employed. According to the disclosure herein, the alkyl group of the esters may be either fluorinated or perfluorinated, i.e. some or all of the hydrogen atoms of the alkyl group are substituted with fluorine atoms.

Examples of amides of the acid monomers that may be mentioned are (meth)acrylamides, for example, N-alkyl (meth)acrylamides, such as $C_2$-$C_{12}$ alkyl. Among the N-alkyl (meth)acrylamides which may be mentioned are N-ethylacrylamide, N-t-butylacrylamide, N-t-octylacrylamide and N-undecylacrylamide.

The vinyl film-forming polymers may also result from the homopolymerization or copolymerization of monomers chosen from vinyl esters and styrene monomers. For example, these monomers may be polymerized with acid monomers and/or esters thereof and/or amides thereof, such as those mentioned above.

Examples of vinyl esters that may be mentioned are vinyl acetate, vinyl neodecanoate, vinyl pivalate, vinyl benzoate and vinyl t-butylbenzoate.

Examples of styrene monomers that may be mentioned are styrene and α-methylstyrene.

Among the possible film-forming polycondensates that may be mentioned are polyurethanes, polyesters, polyesteramides, polyamides, epoxyester resins and polyureas.

The polyurethanes may be chosen from anionic, cationic, nonionic and amphoteric polyurethanes, polyurethane-acrylics, polyurethane-polyvinylpyrrolidones, polyester-polyurethanes, polyether-polyurethanes, polyureas and polyurea/polyurethanes, and mixtures thereof.

The polyesters may be obtained, in a known manner, by polycondensation of dicarboxylic acids with polyols, for example diols.

The dicarboxylic acid may be aliphatic, alicyclic or aromatic. Non-limiting examples of such acids that may be mentioned are: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid and 2,6-naphthalenedicarboxylic acid. These dicarboxylic acid monomers may be used alone or as a combination of at least two dicarboxylic acid monomers. Among these monomers, mention may be made of those chosen from phthalic acid, isophthalic acid and terephthalic acid.

The diol may be chosen from aliphatic, alicyclic and aromatic diols. For example, the diol used may chosen from ethylene glycol, diethylene glycol, triethylene glycol, 1,3-propanediol, cyclohexanedimethanol and 4-butanediol. Other polyols that may be used are glycerol, pentaerythritol, sorbitol and trimethylolpropane.

The polyesteramides may be obtained in a manner analogous to that of the polyesters, by polycondensation of diacids with diamines or amino alcohols. Diamines which may be used include ethylenediamine, hexamethylenediamine and meta- or para-phenylenediamine. An amino alcohol which may be used is monoethanolamine.

The polyester may also comprise at least one monomer bearing at least one group —$SO_3M$, wherein M may be chosen from hydrogen, ammonium ions $NH_4^+$ and metal ions such as, for example, $Na^+$, $Li^+$, $K^+$, $Mg^{2+}$, $Ca^{2+}$, $Cu^{2+}$, $Fe^{2+}$ and $Fe^{3+}$ ions. For instance, a difunctional aromatic monomer comprising such a group —$SO_3M$.

The aromatic nucleus of the difunctional aromatic monomer also bearing a group —$SO_3M$ as described above may be chosen, for example, from benzene, naphthalene, anthracene, biphenyl, oxybiphenyl, sulphonylbiphenyl and methylenebiphenyl nuclei. As suitable non-limiting examples of difunctional aromatic monomers also bearing a group —$SO_3M$, mention may be made of: sulphoisophthalic acid, sulphoterephthalic acid, sulphophthalic acid, 4-sulphonaphthalene-2,7-dicarboxylic acid.

Of the copolymers used, mention may be made of those based on isophthalate/sulphoisophthalate, and for example copolymers obtained by condensation of diethylene glycol, cyclohexanedimethanol, isophthalic acid and sulphoisophthalic acid.

The polymers of natural origin, optionally modified, may be chosen from shellac resin, sandarac gum, dammar resins, elemi gums, copal resins, cellulose polymers, and mixtures thereof.

According to one aspect of the composition disclosed herein, the film-forming polymer may be a water-soluble polymer and may be present in an aqueous phase of the composition; the polymer is thus solubilized in the aqueous phase of the composition. Non-limiting examples of water-soluble film-forming polymers that may be mentioned are:

proteins, for instance proteins of plant origin such as wheat proteins and soybean proteins; proteins of animal origin such as keratins, for example keratin hydrolysates and sulphonic keratins;

polymers of celluloses such as hydroxyethylcellulose, hydroxypropylcellulose, methylcellulose, ethylhydroxyethylcellulose and carboxymethylcellulose, and quaternized cellulose derivatives;

acrylic polymers or copolymers, such as polyacrylates or polymethacrylates;

vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;

polymers of natural origin, which may be optionally modified, such as:
gum arabics, guar gum, xanthan derivatives, karaya gum; alginates and carrageenans;
glycoaminoglycans, hyaluronic acid and derivatives thereof;
shellac resin, sandarac gum, dammar resins, elemi gums and copal resins;
deoxyribonucleic acid;
mucopolysaccharides such as chondroitin sulphate, and mixtures thereof.

According to another aspect of the composition as disclosed herein, the film-forming polymer may be present in a liquid fatty phase comprising organic solvents or oils such as those described above (the film-forming polymer is thus said to be a liposoluble polymer). For the purposes of the disclosure herein, the expression "liquid fatty phase" means a fatty phase which is liquid at room temperature (25° C.) and atmospheric pressure (760 mmHg, i.e. $10^5$ Pa), composed of one or more fatty substances that are liquid at room temperature, also known as oils, which are generally mutually compatible.

The liquid fatty phase may comprise a volatile oil, optionally mixed with a non-volatile oil, the oils possibly being chosen from those mentioned above.

Suitable non-limiting examples of liposoluble polymers which may be mentioned include copolymers of vinyl ester (the vinyl group being directly linked to the oxygen atom of the ester group and the vinyl ester comprising a saturated, linear or branched hydrocarbon-based radical of 1 to 19 carbon atoms, linked to the carbonyl of the ester group) and of at least one other monomer which may be a vinyl ester (other than the vinyl ester already present), an α-olefin (comprising from 8 to 28 carbon atoms), an alkyl vinyl ether (wherein the alkyl group comprises from 2 to 18 carbon atoms) or an allylic or methallylic ester (comprising a saturated, linear or branched hydrocarbon-based radical of 1 to 19 carbon atoms, linked to the carbonyl of the ester group).

These copolymers may be crosslinked with the aid of crosslinking agents, which may be either of the vinyl type or of the allylic or methallylic type, such as tetraallyloxyethane, divinylbenzene, divinyl octanedioate, divinyl dodecanedioate and divinyl octadecanedioate.

Non-limiting examples of these copolymers which may be mentioned are the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetaallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Non-limiting examples of liposoluble film-forming polymers that may also be mentioned are liposoluble copolymers, for example, those resulting from the copolymerization of vinyl esters comprising from 9 to 22 carbon atoms or of alkyl acrylates or methacrylates, and alkyl radicals comprising from 10 to 20 carbon atoms. Such liposoluble copolymers may be chosen from the copolymers of polyvinyl stearate, polyvinyl stearate crosslinked with divinylbenzene, with diallyl ether or with diallyl phthalate, polystearyl (meth)acrylate, polyvinyl laurate and polylauryl (meth)acrylate, it being possible for these poly(meth)acrylates to be crosslinked with the aid of ethylene glycol dimethacrylate or tetraethylene glycol dimethacrylate.

The liposoluble copolymers described above are known and are described in patent application FR-A-2 232 303; they may have a weight-average molecular weight ranging from 2 000 to 500 000, such as from 4 000 to 200 000.

As liposoluble film-forming polymers that may be used in the invention, mention may also be made of polyalkylenes and for example, copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose, copolymers of vinylpyrrolidone (VP) and for example, copolymers of vinylpyrrolidone and of $C_2$ to $C_{40}$ such as, $C_3$ to $C_{20}$ alkenes. Regarding VP copolymers that may be used in the invention, mention may be made of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

The film-forming polymer may also be present in the composition in the form of particles dispersed in an aqueous phase or in a non-aqueous solvent phase, which is generally known as a latex or pseudolatex. The techniques for preparing these dispersions are well known to those of ordinary skill in the art.

Some aqueous dispersions of film-forming polymers which may be used are the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® by the company Daito Kasey Kogyo; or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer; the sulphopolyesters sold under the brand name "Eastman AQ®" by the company Eastman Chemical Products, vinyl dispersions, for instance "Mexomer PAM" and also acrylic dispersions in isododecane, for instance "Mexomer PAP" by the company Chimex.

The composition as disclosed herein may comprise a plasticizer, which promotes the formation of a film with the film-forming polymer. Such a plasticizer may be chosen from any of the compounds known to those skilled in the art as being capable of satisfying the desired function.

Additives

The composition as disclosed herein may also comprise a dyestuff, for instance pulverulent dyestuffs, liposoluble dyes and water-soluble dyes. This dyestuff may be present in a content ranging from 0.01% to 30% by weight, relative to the total weight of the composition.

The pulverulent dyestuffs may be chosen from pigments and nacres.

The pigments may be white or coloured, mineral and/or organic, and coated or uncoated. Suitable non-limiting examples of the mineral pigments that may be mentioned include titanium dioxide, optionally surface-treated, zirconium oxide, zinc oxide or cerium oxide, as well as iron oxide, chromium oxide, manganese violet, ultramarine blue, chromium hydrate and ferric blue. Suitable non-limiting examples of organic pigments that may be mentioned are carbon black, pigments of D & C type, and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica with, for example, ferric blue or chromium oxide, titanium mica with an organic pigment of the abovementioned type, and nacreous pigments based on bismuth oxychloride.

Non-limiting examples of liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto. Suitable non-limiting examples of water-soluble dyes are, for example, beetroot juice, methylene blue, the disodium salt of ponceau, the disodium salt of alizarin green, quinoline yellow, the trisodium salt of amaranthus, the disodium salt of tartrazine, the monosodium salt of rhodamine, the disodium salt of fuchsin, and xanthophyll.

The composition as disclosed herein may also comprise any additive usually used in cosmetics, such as antioxidants, fillers other than the filler with a specific surface area described above, preserving agents, fragrances, neutralizers, thickeners and vitamins, and mixtures thereof.

According to one aspect of the disclosure, the composition does not comprise a UV-screening agent (organic screening agent or mineral screening agent; screening agent that absorbs or reflects ultraviolet radiation).

According to another aspect of the disclosure, the composition is a mascara.

Needless to say, a person of ordinary skill in the art will take care to select the optional additional additives and/or the amount thereof such that the beneficial properties of the composition as disclosed herein are not, or are not substantially, adversely affected by the addition envisaged.

The composition as disclosed herein may be manufactured by the known processes generally used in cosmetics.

The composition as disclosed herein may be packaged in an applicator product comprising a reservoir and a removable means for closing the said reservoir, such as in a leaktight manner.

The said applicator assembly may also comprise a member for applying the makeup composition to the keratin fibres, for instance, the eyelashes, the said applicator member allowing the composition to be taken up and allowing the composition taken up to be deposited on the eyelashes. This applicator member may be securely fastened to the means for leaktight closure of the assembly.

The applicator assembly may also comprise a draining member (or drainer) for the said applicator member, the draining member possibly being securely fastened to the reservoir.

The applicator member may be a mascara brush that is well known to those of ordinary skill in the art. Such a brush may comprise bristles arranged radially around a twisted core, for instance a metal core. The brush may be of varied shape and may comprise cutout sections. Mascara brushes are described, for example, in documents FR-A-2 607 373, EP-A-611 170, EP-A-811 336, EP-A-811 337 and EP-A-842 620.

FIG. 1, to which reference is now made, shows one embodiment of a packaging and applicator assembly 1 comprising a composition for coating keratin fibres as disclosed herein.

The packaging and applicator assembly 1 comprises a container 2 on which is mounted a threaded neck 3, one free edge of which delimits an aperture 4. In the aperture 4 is mounted a draining member 5. The assembly 1 also comprises an applicator device 10 comprising a cap 11 securely fastened to a stem 13, one end of which comprises an applicator 12, generally configured in the form of an arrangement of fibres held between the two branches of a twisted iron wire. An inner surface of the cap 11 is threaded so as to engage with the threading of the neck 3. Thus, when the applicator 12 and the stem 13 are placed inside the container 2, the threading of the cap 11 engages with the threading of the neck 3 such that the cap closes the aperture 4 of the container in a leaktight manner.

Alternatively, the applicator may comprise a comb generally comprising a plurality of teeth obtained by moulding with a support made of thermoplastic material. The applicator may also combine a comb with a brush.

The invention is illustrated in greater detail in the examples that follow.

EXAMPLES 1 to 6

An anhydrous mascara according to the disclosure herein (Example 1) and 5 mascaras not forming part of the invention (Examples 2 to 6) having the composition below were prepared, using 6 different waxes:

| | |
|---|---|
| wax | 27 g |
| bentonite | 5.3 g |
| propylene carbonate | 1.7 g |
| vinyl acetate/allyl stearate copolymer (65/35) (Mexomer PQ from Chimex) | 2.2 g |
| polyvinyl laurate (Mexomer PP from Chimex) | 0.7 g |
| silica | 0.8 g |
| pigments | 3.6 g |
| preserving agents | qs |
| isododecane | qs 100 g |

For each composition, the viscosity and the consistency index were measured, and the stability at 25° C. was evaluated.

The viscosity measurement was performed at 25° C. using a Rheomat RM 180 viscometer equipped with a No. 4 spindle, the measurement was performed after rotation of the spindle for 10 minutes (after which time stabilization of the viscosity and of the rotation speed of the spindle were observed), at a shear rate of 200 s$^{-1}$.

The consistency index measurement is performed using a TA-XT2i texturometer from the company Rheo, equipped with a stainless-steel cylindrical probe 12 mm in diameter.

A cylindrical container (35 mm in diameter and 15 mm deep) was filled with the mascara composition to be tested and the surface of the product contained in the container was then leveled off to obtain a totally flat surface of the product. The cylindrical probe of the texturometer was displaced at a speed of 10 mm·s$^{-1}$ and then penetrated the mascara contained in the cylindrical container, to a depth of 0.2 mm. The force exerted by the mascara on the probe was then measured, this force corresponding to the consistency index of the mascara, expressed in Pa.

The stability was evaluated by visual observation of the composition after storage for two weeks at 25° C.

The tack and the hardness of the wax were measured according to the measuring method described previously in the description.

The following results were obtained:

| Example | Wax | Tack (N·s) | Hardness (MPa) | Viscosity (Pa·s) | Consistency (Pa) | Stability |
|---|---|---|---|---|---|---|
| 1 | Koster K 82 P | 3.38 | 0.96 | 3.6 | 560 | Yes |
| 2 | Beeswax | 2.02 | 3.68 | 5.9 | 1 842 | Yes |
| 3 | Hydrogenated jojoba oil | 0.18 | 8.62 | 12.8 | 1 991 | Yes |
| 4 | Hydrogenated castor oil | 0.08 | 2.77 | Too thick | 22 942 | — |
| 5 | Orange oil[(1)] | 0.09 | 0.09 | <1 | Too fluid | No 2 phases |
| 6 | Oxypropylenated (5 PO) lanolin wax[(2)] | 0.14 | 0.06 | <1 | Too fluid | No 2 phases |

[(1)]sold by the company Koster Keunen
[(2)]Emery 1695 from the company Cognis

It was found that composition 1 according to the disclosure herein was stable and had the lowest viscosity and the lowest consistency. Compositions 2 and 3, although stable, had a higher viscosity and a higher consistency than those of composition 1. Composition 4 was too thick and was therefore unsuitable for application to the eyelashes using a mascara brush.

Compositions 5 and 6 were not stable: they showed 2 phases after two weeks of storage at 25° C.

EXAMPLE 7

A wax-in-water emulsion mascara having the composition below was prepared:

| | |
|---|---|
| tacky wax (Kester Wax K 82 P from the company Koster Keunen) | 30 g |
| 2-amino-2-methyl-1,3-propanediol | 0.5 g |
| triethanolamine | 2.4 g |
| stearic acid | 5.8 g |
| water-soluble nonionic polymers | 4.3 g |
| sodium polymethacrylate (Darvan 7 from the company Vanderbilt) | 0.25 g AM |
| hydroxyethylcellulose crosslinked with epichlorohydrin, quaternized with trimethylamine (JR 400 from the company Union Carbide) | 0.1 g |
| pigments | 5.4 g |
| preserving agents | qs |
| water | qs 100 g |

This mascara was stable after 24 hours at room temperature. It applied easily and adhered well to the eyelashes. The mascara formed a smooth, uniform makeup and thickened the eyelashes.

EXAMPLE 8

An anhydrous mascara having the composition below was prepared:

| | |
|---|---|
| tacky wax (Kester Wax K 82 P from the company Koster Keunen) | 30 g |
| bentonite | 5.3 g |
| propylene carbonate | 1.7 g |
| vinyl acetate/allyl stearate copolymer (65/35) (Mexomer PQ from Chimex) | 2.2 g |
| polyvinyl laurate (Mexomer PP from Chimex) | 0.7 g |
| stearate of the oligomer of 12-hydroxy-stearic acid (Solsperse 21000 from Avecia) | 0.1 g |
| silica | 0.8 g |
| pigments | 4.2 g |
| preserving agents | qs |
| isododecane | qs 100 g |

This waterproof mascara adhered well to the eyelashes. It gave the eyelashes a highly separated, smooth, uniform makeup.

EXAMPLE 9

An anhydrous mascara having the composition below was prepared:

| | |
|---|---|
| tacky wax (Kester Wax K 82 P from the company Koster Keunen) | 35 g |
| bentonite | 5.3 g |
| propylene carbonate | 1.7 g |
| vinyl acetate/allyl stearate copolymer (65/35) (Mexomer PQ from Chimex) | 2.2 g |
| polyvinyl laurate (Mexomer PP from Chimex) | 0.7 g |
| stearate of the oligomer of 12-hydroxy-stearic acid (Solsperse 21000 from Avecia) | 0.1 g |
| silica | 0.8 g |
| pigments | 4.2 g |
| preserving agents | qs |
| isododecane | qs 100 g |

This waterproof mascara adhered well to the eyelashes. It gave the eyelashes a highly separated, smooth, uniform makeup.

EXAMPLE 10

A wax-in-water emulsion mascara having the composition below was prepared:

| | |
|---|---|
| tacky wax (Kester Wax K 82 P from the company Koster Keunen) | 15 g |
| microcrystalline wax | 10 g |
| 2-amino-2-methyl-1,3-propanediol | 0.5 g |
| triethanolamine | 2.4 g |
| stearic acid | 5.8 g |
| water-soluble nonionic polymers | 4.3 g |
| sodium polymethacrylate (Darvan 7 from the company Vanderbilt) | 0.25 g AM |
| hydroxyethylcellulose crosslinked with epichlorohydrin, quaternized with trimethyl-amine (JR 400 from the company Union Carbide) | 0.1 g |
| pigments | 5.4 g |
| preserving agents | qs |
| water | qs 100 g |

This mascara adhered well to the eyelashes.
The makeup was smooth and uniform.

EXAMPLE 11

A wax-in-water emulsion mascara having the composition below was prepared:

| | |
|---|---|
| tacky wax (Kester Wax K 82 P from the company Koster Keunen) | 25 g |
| candellila wax | 6 g |
| 2-amino-2-methyl-1,3-propanediol | 0.5 g |
| triethanolamine | 2.4 g |
| stearic acid | 5.8 g |
| isononyl isononanoate | 3 g |
| water-soluble nonionic polymers | 4.3 g |
| pigments | 5.4 g |
| preserving agents | qs |
| water | qs 100 g |

This mascara was easily applied to the eyelashes and the makeup of the eyelashes was smooth and uniform.

EXAMPLE 12

A wax-in-water emulsion mascara having the composition below was prepared:

| | |
|---|---|
| tacky wax (Kester Wax K 82 P from the company Koster Keunen) | 25 g |
| Carnauba wax | 3 g |
| 2-amino-2-methyl-1,3-propanediol | 0.5 g |
| triethanolamine | 2.4 g |
| stearic acid | 5.8 g |
| water-soluble nonionic polymers | 4.3 g |
| pigments | 5.4 g |
| preserving agents | qs |
| water | qs 100 g |

This mascara adhered well to the eyelashes.
The makeup was smooth and uniform.

EXAMPLE 13

An anhydrous mascara having the composition below was prepared:

| | |
|---|---|
| tacky wax (Kester Wax K 82 P from the company Koster Keunen) | 17.5 g |
| microcrystalline wax | 17.5 g |
| bentonite | 5.3 g |
| propylene carbonate | 1.7 g |
| vinyl acetate/allyl stearate copolymer (65/35) (Mexomer PQ from Chimex) | 2.2 g |
| polyvinyl laurate (Mexomer PP from Chimex) | 0.7 g |
| stearate of the oligomer of 12-hydroxy-stearic acid (Solsperse 21000 from Avecia) | 0.1 g |
| talc | 0.8 g |
| pigments | 4.2 g |
| preserving agents | qs |
| isododecane | qs 100 g |

This waterproof mascara adhered well to the eyelashes. It gave the eyelashes a highly separated, smooth, uniform makeup.

EXAMPLES 14 TO 16

The anhydrous mascaras below were prepared:

| | |
|---|---|
| tacky wax (Kester Wax K 82 P ® from the company Koster Keunen) | 27 g |
| bentonite | 2.66 g |
| propylene carbonate | 1.7 g |
| vinyl acetate/allyl stearate copolymer (65/35) (Mexomer PQ ® from Chimex) | 2.2 g |
| polyvinyl laurate (Mexomer PP ® from Chimex) | 0.7 g |
| stearate of the oligomer of 12-hydroxy-stearic acid (Solsperse 21000 ® from Avecia) | 0.1 g |
| filler with a specific surface area | 15 g |
| pigments | 4.2 g |
| preserving agents | qs |
| isododecane | qs 100 g |

Using this formulation, three different mascaras in accordance with the disclosure herein were prepared, incorporating a specific filler into each of them.

The nature of the three fillers chosen, their specificities and the respective amounts are given in Table 1.

The silica Sunsil 130® is sold by Sunjin Chemical.

The polymethyl methacrylate Jurymer MB1® is sold by Nihon Junyakuet, and the silica Sunsphere H-51® is sold by Asahi Glass.

The tack was evaluated according to the following protocol:

A sample comprising straight hairs (60 hairs 15 mm long) was made up by applying the product in 30 successive sweeps with a brush. After drying for one hour, the made-up hairs were rubbed with a finger, by means of a to and fro motion. The tack was assessed qualitatively according to the degree of stuck hairs, from 1 (not stuck at all) to 5 (very stuck).

The three waterproof mascaras thus obtained adhered well to the eyelashes. They gave the eyelashes a highly separated, smooth, uniform makeup.

EXAMPLE 17

An anhydrous waterproof mascara having the composition below was prepared:

| | |
|---|---|
| Tacky wax (Kester Wax K 82 P ® from the company Koster Keunen) | 32 g |
| Dextrin palmitate (Rheopearl KL ® from Chiba Flour) | 5.3 g |
| Vinyl acetate/allyl stearate copolymer (65/35) (Mexomer PQ ® from Chimex) | 2.2 g |
| Polyvinyl laurate (Mexomer PP ® from Chimex) | 0.75 g |
| Stearate of the oligomer of 12-hydroxystearic acid (Solsperse 21000 ® from Avecia) | 0.1 g |
| Silica | 10 g |
| Talc | 0.84 g |
| Pigments | 4.6 g |
| Preserving agents | qs |
| Isododecane | 100 g |

The mascara applied easily to the eyelashes and gaves the eyelashes a thick, non-tacky makeup: the eyelashes were well separated.

EXAMPLE 18

A wax/water emulsion mascara having the composition below was prepared:

| | |
|---|---|
| Tacky wax (Kester Wax K 82 p ® from the company Koster Keunen) | 25 g |
| Candelilla wax | 3 g |
| Dextrin palmitate (Rheopearl KL ® from Chiba Flour) | 6 g |
| Stearic acid | 5.8 g |
| 2-Amino-2-methyl-1,3-propanediol | 0.5 g |
| Triethanolamine | 2.4 g |
| Hydroxyethylcellulose | 0.9 g |
| Silica | 5 g |
| Pigments | 5.5 g |
| Preserving agents | qs |
| Water | qs 100 g |

The mascara applied very easily to the eyelashes and gave a charging and separating uniform deposit.

TABLE 1

| Example (Formula) | Trade name | Chemical nature | Mass (g) | Size of the filler μm | Specific surface area m²/g | Tack after rubbing on samples |
|---|---|---|---|---|---|---|
| No. 1 | Sunsil 130 ® | Hollow and spherical silica | 15 | 6-9 | 200-260 | 1 |
| No. 2 | Jurymer MB1 ® | polymethyl methacrylate | 15 | 8-15 | 300 | 2 |
| No. 3 | Sunsphere ® H-51 | Hollow silica microspheres | 15 | 5 | 770 | 1 |

What is claimed is:

1. A non-therapeutic process for obtaining a uniform and/or smooth and/or separating makeup result on eyelashes comprising applying to the eyelashes a composition comprising, in a cosmetically acceptable medium, at least one wax having a tack of greater than or equal to 0.7 N.s and a hardness of less than or equal to 3.5 MPa, and wherein the at least one wax is a compound of formula (I):

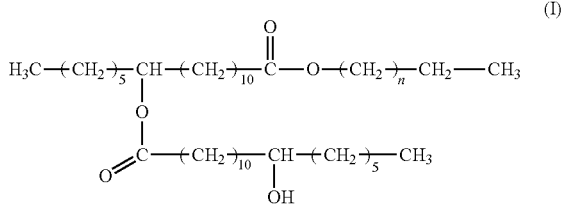

wherein n is an integer ranging from 18 to 38.

2. The non-therapeutic process according to claim 1, wherein the at least one wax has a tack ranging from 0.7 N.s to 30 N.s.

3. The non-therapeutic process according to claim 2, wherein the at least one wax has a tack of greater than or equal to 1 N.s.

4. The non-therapeutic process according to claim 3, wherein the at least one wax has a tack ranging from 1 N.s to 20 N.s.

5. The non-therapeutic process according to claim 4, wherein the at least one wax has a tack of greater than or equal to 2 N.s.

6. The non-therapeutic process according to claim 5, wherein the at least one wax has a tack ranging from 2 N.s to 10 N.s.

7. The non-therapeutic process according to claim 1, wherein the at least one wax has a hardness ranging from 0.01 to 3.5 MPa.

8. The non-therapeutic process according to claim 7, wherein the at least one wax has a hardness ranging from 0.05 MPa to 3 MPa.

9. The non-therapeutic process according to claim 8, wherein the at least one wax has a hardness ranging from 0.1 MPa to 2.5 MPa.

10. The non-therapeutic process according to claim 1, wherein the at least one wax is present in an amount ranging from 0.5% to 60% by weight, relative to the total weight of the composition.

11. The non-therapeutic process according to claim 10, wherein the at least one wax is present in an amount ranging from 5% to 50% by weight, relative to the total weight of the composition.

12. The non-therapeutic process according to claim 11, wherein the at least one wax is present in an amount ranging from 10% to 40% by weight, relative to the total weight of the composition.

13. The non-therapeutic process according to claim 12, wherein the at least one wax is present in an amount greater than 25% by weight, relative to the total weight of the composition.

14. The non-therapeutic process according to claim 13, wherein the at least one wax is present in an amount greater than 27% by weight, relative to the total weight of the composition.

15. The non-therapeutic process according to claim 14, wherein the at least one wax is present in an amount greater than 28% by weight, relative to the total weight of the composition.

16. The non-therapeutic process according to claim 15, wherein the at least one wax is present in an amount greater than 30% by weight, relative to the total weight of the composition.

17. The non-therapeutic process according to claim 1, wherein the composition further comprises at least one additional wax having a hardness of greater than or equal to 6 MPa.

18. The non-therapeutic process according to claim 17, wherein the at least one additional wax has a hardness ranging from 6 MPa to 30 MPa.

19. The non-therapeutic process according to claim 18, wherein the at least one additional wax has a hardness ranging from 7 MPa to 25 MPa.

20. The non-therapeutic process according to claim 19, wherein the at least one additional wax has a hardness ranging from 8 MPa to 25 MPa.

21. The non-therapeutic process according to claim 20, wherein the at least one additional wax has a hardness ranging from 9 to 20 MPa.

22. The non-therapeutic process according to claim 21, wherein the at least one additional wax has a hardness ranging from 10 MPa to 20 MPa.

23. The non-therapeutic process according to claim 17, wherein the at least one additional wax is chosen from carnauba wax, polyethylene waxes, candelilla wax, hydrogenated jojoba oil, bis(1,1,1-trimethylolpropane) tetrastearate, and a wax obtained by hydrogenation of olive oil esterified with stearyl alcohol.

24. The non-therapeutic process according to claim 17, wherein the at least one additional wax is present in an amount ranging from 0.1% to 30% by weight, relative to the total weight of the composition.

25. The non-therapeutic process according to claim 24, wherein the at least one additional wax is present in an amount ranging from 1% to 20% by weight, relative to the total weight of the composition.

26. The non-therapeutic process according to claim 25, wherein the at least one additional wax is present in an amount ranging from 2% to 10% by weight, relative to the total weight of the composition.

27. The non-therapeutic process according to claim 1, wherein the composition further comprises an aqueous phase.

28. The non-therapeutic process according to claim 27, wherein the aqueous phase is chosen from aqueous phases formed from water and aqueous phases formed from a mixture of water and water-miscible organic solvent.

29. The non-therapeutic process according to claim 28, wherein the water-miscible organic solvent is chosen from lower monoalcohols comprising from 1 to 5 carbon atoms, glycols comprising from 2 to 8 carbon atoms, $C_3$-$C_a$ ketones, and $C_2$-$C_4$ aldehydes.

30. The non-therapeutic process according to claim 28, wherein the aqueous phase is present in an amount ranging from 1% to 95% by weight, relative to the total weight of the composition.

31. The non-therapeutic process according to claim 30, wherein the aqueous phase is present in an amount ranging from 3% to 80% by weight, relative to the total weight of the composition.

32. The non-therapeutic process according to claim 31, wherein the aqueous phase is present in an amount ranging from 5% to 60% by weight, relative to the total weight of the composition.

33. The non-therapeutic process according to claim 1, wherein the composition further comprises at least one volatile oil.

34. The non-therapeutic process according to claim 33, wherein the at least one volatile oil is chosen from hydrocarbon-based oils and silicone oils.

35. The non-therapeutic process according to claim 33, wherein the at least one volatile oil is present in an amount ranging from 0.1% to 98% by weight, relative to the total weight of the composition.

36. The non-therapeutic process according to claim 35, wherein the at least one volatile oil is present in an amount ranging from 1% to 65% by weight, relative to the total weight of the composition.

37. The non-therapeutic process according to claim 1, wherein the composition further comprises at least one non-volatile oil.

38. The non-therapeutic process according to claim 37, wherein the at least one non-volatile oil is present in an amount ranging from 0.1% to 30% by weight, relative to the total weight of the composition.

39. The non-therapeutic process according to claim 38, wherein the at least one non-volatile oil is present in an amount ranging from 0.1% to 20% by weight, relative to the total weight of the composition.

40. The non-therapeutic process according to claim 39, wherein the at least one non-volatile oil is present in an amount ranging from 0.1% to 10% by weight, relative to the total weight of the composition.

41. The non-therapeutic process according to claim 1, wherein the composition further comprises at least one film-forming polymer.

42. The non-therapeutic process according to claim 41, wherein the at least one film-forming polymer is present in a solids content ranging from 0.1% to 60% by weight, relative to the total weight of the composition.

43. The non-therapeutic process according to claim 42, wherein the at least one film-forming polymer is present in a solids content ranging from 0.5% to 40% by weight, relative to the total weight of the composition.

44. The non-therapeutic process according to claim 43, wherein the at least one film-forming polymer is present in a solids content ranging from 1% to 30% by weight, relative to the total weight of the composition.

45. The non-therapeutic process according to claim 1, wherein the composition further comprises at least one additional wax.

46. The non-therapeutic process according to claim 45, wherein the at least one additional wax is present in the composition in an amount ranging from 0.1% to 50% by weight, relative to the total weight of the composition.

47. The non-therapeutic process according to claim 46, wherein the at least one additional wax is present in the composition in an amount ranging from 0.5% to 30% by weight, relative to the total weight of the composition.

48. The non-therapeutic process according to claim 47, wherein the at least one additional wax is present in the composition in an amount ranging from 1% to 20% by weight, relative to the total weight of the composition.

49. The non-therapeutic process according to claim 1, wherein the composition further comprises at least one surfactant.

50. The non-therapeutic process according to claim 1, wherein the composition further comprises at least one additive chosen from dyestuffs, antioxidants, fillers, pasty fatty substances, preserving agents, fragrances, neutralizers, thickeners, vitamins, coalescence agents, and plasticizers.

51. The non-therapeutic process according to claim 1, wherein the composition does not comprise a UV-screening agent.

* * * * *

UNITED STATES PATENT AND TRADEMARK OFFICE
CERTIFICATE OF CORRECTION

| | | |
|---|---|---|
| PATENT NO. | : 7,923,002 B2 | Page 1 of 1 |
| APPLICATION NO. | : 10/654887 | |
| DATED | : April 12, 2011 | |
| INVENTOR(S) | : Valérie De La Poterie et al. | |

It is certified that error appears in the above-identified patent and that said Letters Patent is hereby corrected as shown below:

Claim 29, col. 24, line 58, "$C_3$-$C_a$ ketones" should read
-- $C_3$-$C_4$ ketones --.

Signed and Sealed this
Thirty-first Day of May, 2011

David J. Kappos
*Director of the United States Patent and Trademark Office*